(12) United States Patent
Ding et al.

(10) Patent No.: US 6,993,389 B2
(45) Date of Patent: Jan. 31, 2006

(54) IDENTIFYING HEART FAILURE PATIENTS SUITABLE FOR RESYNCHRONIZATION THERAPY USING QRS COMPLEX WIDTH FROM AN INTRACARDIAC ELECTROGRAM

(75) Inventors: Jing Ding, Maplewood, MN (US); Yinghong Yu, Maplewood, MN (US); Julio Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 499 days.

(21) Appl. No.: 10/008,397

(22) Filed: Dec. 6, 2001

(65) Prior Publication Data

US 2002/0143264 A1 Oct. 3, 2002

Related U.S. Application Data

(63) Continuation-in-part of application No. 09/822,638, filed on Mar. 30, 2001, now Pat. No. 6,705,999, and a continuation-in-part of application No. 09/822,790, filed on Mar. 30, 2001, now Pat. No. 6,766,189.

(51) Int. Cl.
    *A61N 1/18* (2006.01)

(52) U.S. Cl. ........................................ 607/25

(58) Field of Classification Search ................ 600/509, 600/516; 607/9, 25
See application file for complete search history.

(56) References Cited

U.S. PATENT DOCUMENTS

| | | | |
|---|---|---|---|
| 3,768,487 A | | 10/1973 | Rose |
| 4,458,691 A | * | 7/1984 | Netravali ................ 600/518 |
| 5,469,858 A | | 11/1995 | Osborne |
| 5,544,661 A | * | 8/1996 | Davis et al. ............. 600/513 |
| 5,634,469 A | | 6/1997 | Bruder et al. |
| 5,694,942 A | | 12/1997 | Escalona |
| 5,740,808 A | | 4/1998 | Panescu et al. |
| 5,827,196 A | | 10/1998 | Yeo et al. |
| 6,115,630 A | | 9/2000 | Stadler et al. |
| 6,144,880 A | | 11/2000 | Ding et al. |

\* cited by examiner

*Primary Examiner*—Mark Bockelman
(74) *Attorney, Agent, or Firm*—Merchant & Gould

(57) ABSTRACT

Methods and systems are disclosed for determining whether a patient is a responder to cardiac resynchronization therapy. The beginning and ending of the intrinsic ventricular depolarization are determined through signals measured from one or more electrodes implanted in the patient's heart. An interval between the beginning and ending of the intrinsic ventricular depolarization is computed and is compared to a threshold. The threshold may be determined empirically. The pacing parameters of a heart stimulation device, such as a pacemaker, may then be configured, for example, by setting the paced atrio-ventricular delay based on whether the patient responds positively to cardiac resynchronization therapy.

43 Claims, 7 Drawing Sheets

IDENTIFYING HEART FAILURE PATIENTS SUITABLE FOR RESYNCHRONIZATION THERAPY USING QRS COMPLEX WIDTH FROM AN INTRACARDIAC ELECTROGRAM

RELATED APPLICATIONS

The present application is a continuation-in-part of the application entitled METHOD AND APPARATUS FOR PREDICTING ACUTE RESPONSE TO CARDIAC RESYNCHRONIZATION THERAPY, having U.S. Ser. No. 09/822,790 filed on Mar. 30, 2001, now U.S. Pat. No. 6,766,189 and is also a continuation-in-part of the application entitled METHOD AND APPARATUS FOR DETERMINING THE CORONARY SINUS VEIN BRANCH ACCESSED BY A CORONARY SINUS LEAD, with U.S. Ser. No. 09/822,638 also filed on Mar. 30, 2001, now U.S. Pat. No. 6,705.999.

TECHNICAL FIELD

The present invention is directed to cardiac resynchronization therapy. More specifically, the present invention is directed to methods and systems for detecting whether patients are responders to ventricular resynchronization therapy.

BACKGROUND

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117. Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. When the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atriums 106, 110 contract to force blood into the right and left ventricles 108, 112, respectively. Typically, the cardiac cycle occurs at a frequency between 60 and 100 cycles per minute and can vary depending on physical exertion and/or emotional stimuli, such as, pain or anger.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (e.g., the sinoatrial node) and a ventricular node 122 (e.g., the atrioventricular node). The sinoatrial node 120 initiates an electrical impulse that spreads through the muscle tissues of the right and left atriums 106, 110 and the atrioventricular node 122. As a result, the right and left atriums 106, 110 contract to pump blood into the right and left ventricles 108, 112 as discussed above. At the atrioventricular node 122, the electrical signal is momentarily delayed before propagating through the right and left ventricles 108, 112. Within the right and left ventricles 108, 112, the conduction system includes right and left bundle branches 126, 128 that extend from the atrioventricular node 122 via the Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106, 110 contract (e.g., atrial contractions) and relax synchronously. Shortly after the atrial contractions, both the right and left ventricles 108, 112 contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relaxations and filling. In situations where the blockage is in the ventricles (e.g., the right and left bundle branches 126, 128), the right and/or left ventricles 108, 112 can only be excited through slow muscle tissue conduction. As a result, the muscular walls of the affected ventricle (108 and/or 112) do not contract synchronously (e.g., asynchronous contraction), thereby, reducing the overall effectiveness of the heart 100 to pump oxygen-rich blood throughout the body. For example, asynchronous contraction of the left ventricular muscles can degrade the global contractility (e.g., the pumping power) of the left ventricle 112 which can be measured by the peak ventricular pressure change during systole (denoted as "LV+dp/dt"). A decrease in LV+dp/dt corresponds to a worsened pumping efficiency and less cardiac output.

Similarly, heart valve disorders (e.g., valve regurgitation or valve stenosis) can interfere with the heart's 100 ability to pump blood, thereby, reducing stroke volume (i.e., aortic pulse pressure) and/or cardiac output.

Various medical procedures have been developed to address these and other heart disorders. In particular, cardiac resynchronization therapy ("CRT") can be used to improve the conduction pattern and sequence of mechanical contractions of the heart. CRT involves the use of an artificial electrical stimulator that is surgically implanted within the patient's body. Leads from the stimulator can be affixed at a desired location within the heart to effectuate synchronous atrial and/or ventricular contractions. Typically, the location of the leads (e.g., stimulation site) is selected based upon the severity and/or location of the blockage. Electrical stimulation signals can be delivered to resynchronize the heart, thereby, improving cardiac performance.

Despite these advantages, several shortcomings exist that limit the usefulness of CRT. For example, results from many clinical studies have shown that hemodynamic response to CRT typically varies from patient to patient, ranging from very positive (e.g., improvement) to substantially negative (e.g., deterioration). Thus, in order to predict the benefit from CRT, the patient typically must be screened prior to receiving the therapy. One common method that predicts hemodynamic response to CRT relies on measurement of a surface electrocardiagram (ECG). Such measurement is often performed manually and is subject to human error. Additionally, it is difficult to implement such a surface measurement with an implantable device thereby making it difficult to continuously monitor the response.

Thus, there is a need for improved methods and systems that can automatically and reliably predict whether a patient will have a positive response to CRT and/or be able to monitor the response continuously during the entire course of CRT.

SUMMARY

Embodiments of the present invention provide methods and systems that detect whether a patient is a responder to CRT. The methods and systems involve making measurements with at least one electrode implanted within the patient's heart. An implanted heart stimulation device, external device programmer, or other device may then determine from the measurements whether the patient will have a positive response to CRT.

The present invention may be viewed as a method for determining whether a patient is a responder to resynchronization therapy. The method involves detecting a beginning of an intrinsic ventricular depolarization with an electrode positioned at a ventricle of the heart of the patient. An ending of the intrinsic ventricular depolarization is also detected. An interval between the beginning of the intrinsic ventricular depolarization and the ending of the intrinsic ventricular depolarization is measured. The interval is then compared to a threshold.

The present invention may also be viewed as a system for determining whether a patient is a responder to resynchronization therapy. The system includes an electrode positioned at a ventricle of the heart of the patient. A detection module is communicatively linked to the electrode, and the detection module detects a beginning of an intrinsic ventricular depolarization and an ending of the intrinsic ventricular depolarization. The system also includes a processing module communicatively linked to the detection module, wherein the processing module computes an interval between the beginning of the intrinsic ventricular depolarization and the ending of the intrinsic ventricular depolarization and compares the interval to a threshold.

The present invention may also be viewed as another system for determining whether a patient is a responder to resynchronization therapy. The system includes means for detecting a beginning of an intrinsic ventricular depolarization and an ending of the intrinsic ventricular depolarization. Additionally, the system includes means for computing an interval between the beginning of the intrinsic ventricular depolarization and the ending of the intrinsic ventricular depolarization and for comparing the interval to a threshold.

DETAILED DESCRIPTION

Figure 1:
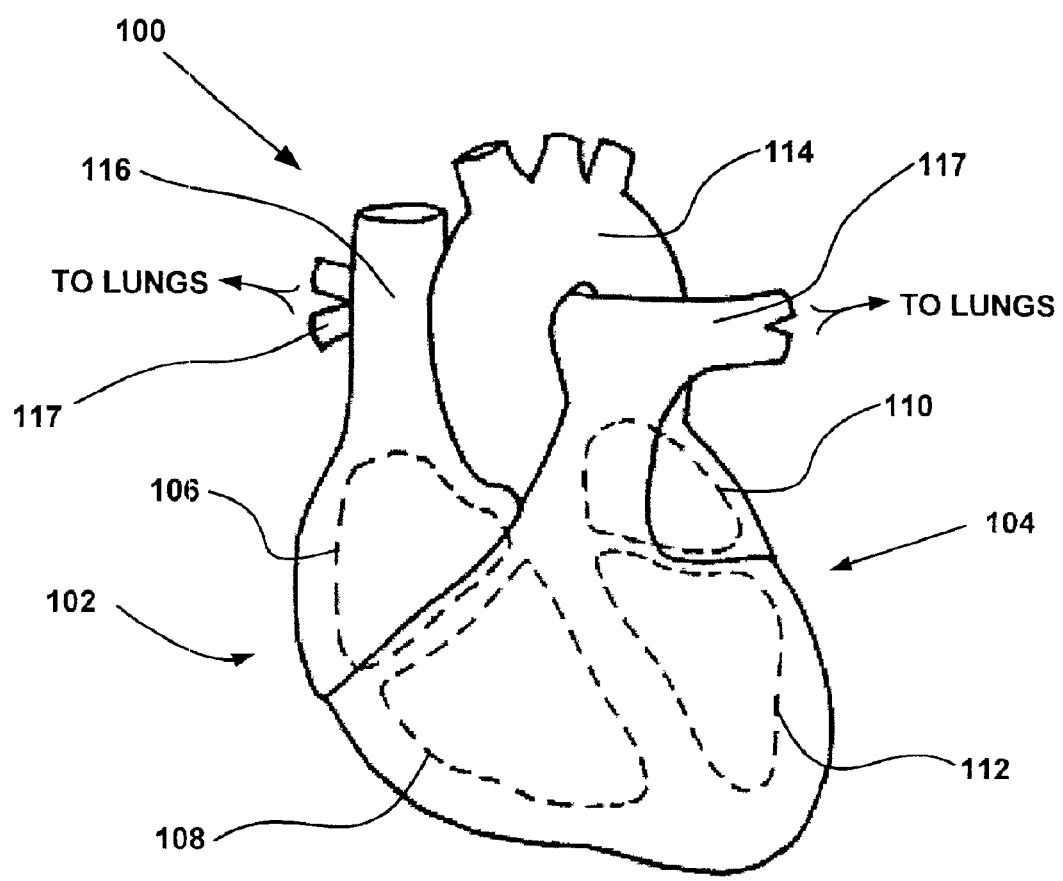
FIG. 1 is a diagram showing the various chambers of the heart.
Figure 2:
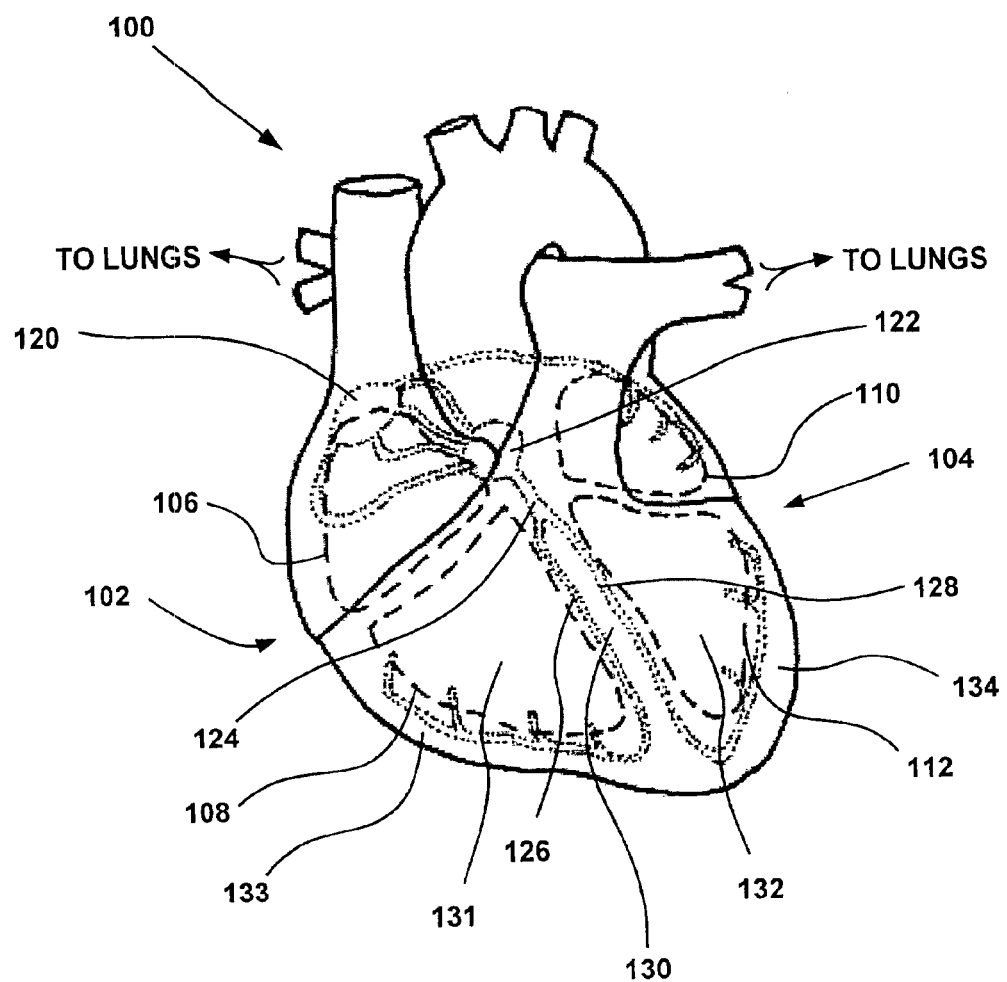
FIG. 2 is a diagram showing the various chambers and the electrical conduction system of the heart.

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a suitable method for predicting whether a patient will positively respond to cardiac resynchronization therapy ("CRT"). As will be described in greater detail below, the method of the present disclosure predicts a patient's response to CRT by measuring and comparing an intrinsic ventricular depolarization period against a threshold. As will become apparent from the discussion below in connection with the various drawings, the ventricular depolarization period may be measured by finding a beginning and ending of the depolarization through processing of an intracardiac signal to find a beginning value Q* and an ending value S*. However, those of ordinary skill in the art will readily appreciate that the method of the present disclosure can be implemented using any suitable beginning and ending value, which may or may not be found by employing various methods for measuring Q* and S*.

In a preferred embodiment, the method of the present disclosure predicts whether a patient will respond to CRT by evaluating the period of depolarization of the right or left ventricles 108, 112 (FIG. 1). The period of depolarization of the ventricles 108, 112 can be evaluated using an intracardiac electrogram. An intracardiac electrogram is generally a graphical depiction of the electrical depolarization or excitement of the heart 100 (FIG. 1) that is measured by one or more electrodes placed on or within the heart 100, such as within the right or left ventricles.

Figure 3:
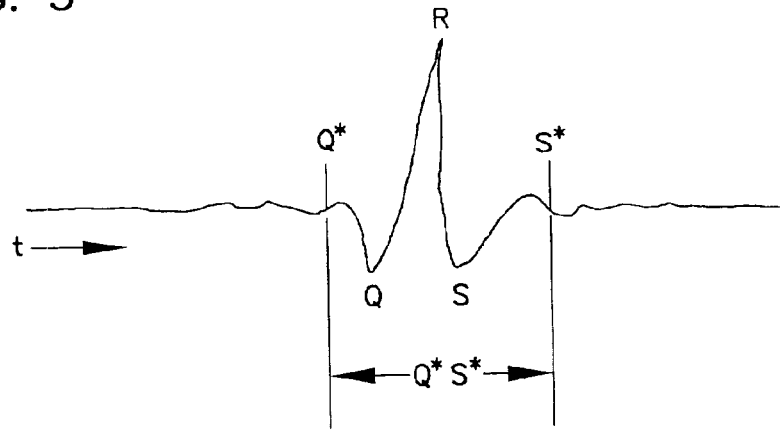
FIG. 3 is a graph showing ventricular depolarization as a function of time.

An exemplary electrogram for an intrinsic systolic cycle is shown in FIG. 3. Each portion of the electrogram is typically given an alphabetic designation corresponding to a predetermined period of electrical depolarization or excitement. For example, the portion of the electrogram that represents atrial depolarization is commonly referred to as the P-wave (not shown). Similarly, the portion of the electrogram that represents ventricular depolarization is commonly referred to as the QRS complex comprising a Q-wave, an R-wave, and an S-wave. Moreover, the portion of the electrogram that represents ventricular recovery or repolarization is commonly referred to as the T-wave (not shown).

As shown in FIG. 3, the QRS complex has a beginning and an ending. To determine the beginning and ending, the intracardiac electrogram may be analyzed, as discussed below, to find various representative values. The representative beginning value Q* and ending value S* are shown in FIG. 3. Other values representative of the beginning and ending of the QRS complex may be used in place of the Q* and S* values that are defined by the calculations discussed below.

Figure 4:
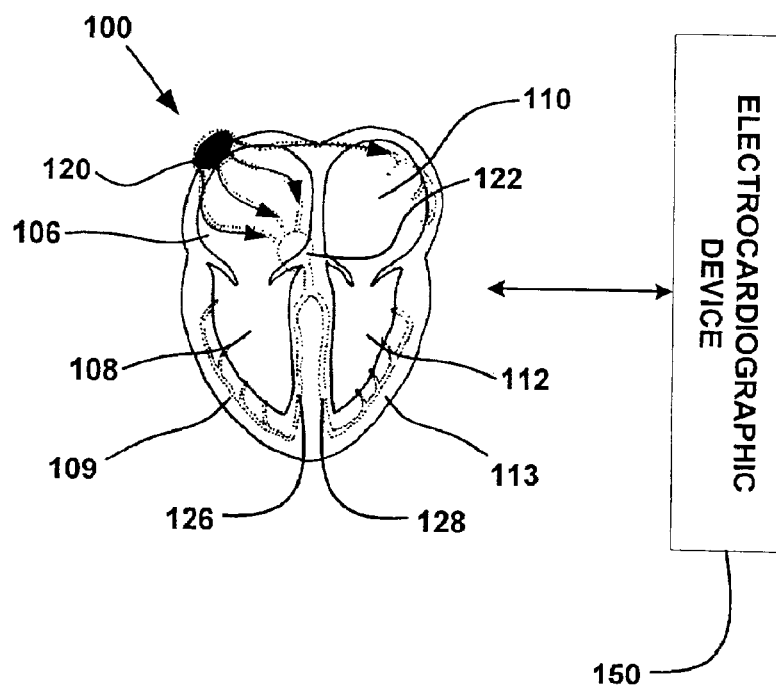
FIGS. 4–6 are diagrams illustrating a heart and the electrical conduction system advancing through a normal cardiac cycle.
Figure 5:
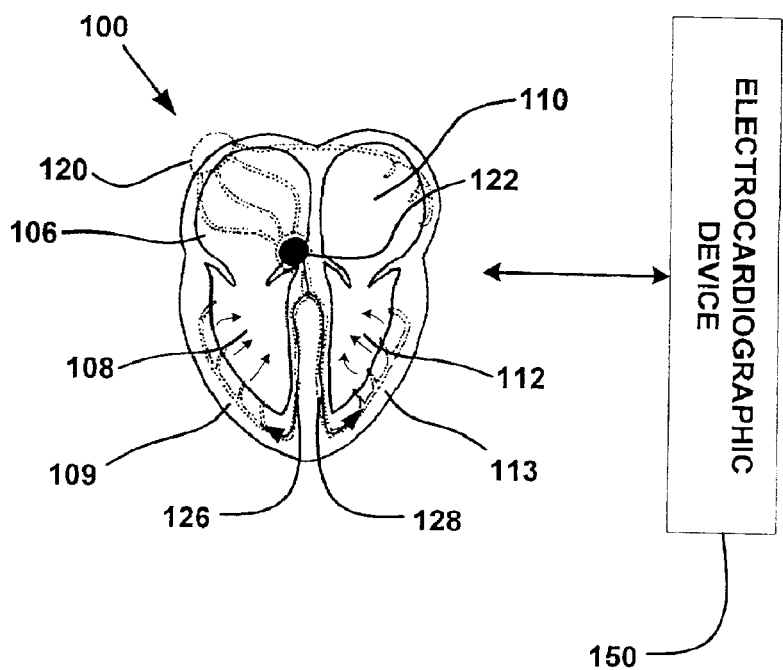
Figure 6:
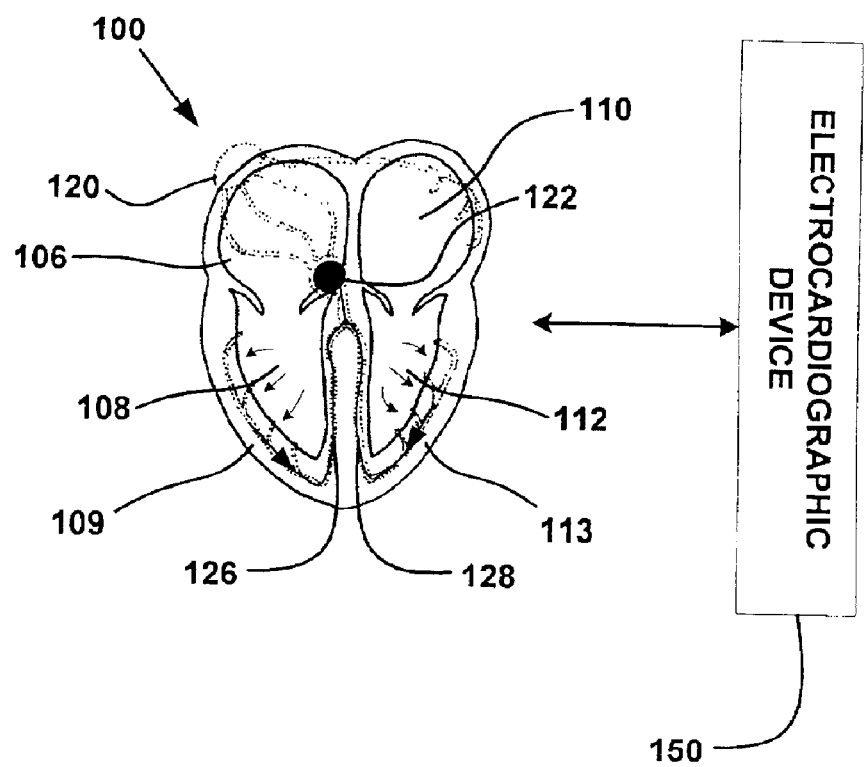

Each period of electrical depolarization or excitement represented on the electrogram corresponds to a period of muscular activation within the heart 100 (FIG. 1). FIGS. 4–6 are schematic illustrations depicting the various periods of muscular activation within the heart 100. As shown in FIGS. 4–6, the electrogram data can be monitored using any suitable electrocardiographic device 150, such as an implantable heart stimulation device (i.e. CRT device), that is connected to leads located on or within the heart 100.

FIG. 4 is a schematic illustration showing the period of atrial activation in response to electrical impulses initiated at the sinoatrial node 120 (corresponding to the P-wave portion as discussed above). After electrical impulses spread from the sinoatrial node 120, the muscle tissues of the right and left atriums 106, 110 contract to pump blood into the right and left ventricles 108, 112, respectively.

FIG. 5 is a schematic illustration showing the period of a ventricular depolarization in response to electrical impulses initiated at the atrioventricular node 122 that spread through the ventricles 108, 112 (corresponding to the QRS portion as discussed above). After electrical impulses spread from the atrioventricular node 122, the muscle tissues of the right and left ventricles 108, 112 contract to pump blood to the lungs and throughout the body, respectively.

FIG. 6 is a schematic illustration showing ventricular recovery or repolarization (corresponding to the T-wave portion as discussed above). During ventricular repolarization, the membrane potential of the muscle cells reverse polarity and return to their resting state, thereby, causing the ventricles to relax.

An electrogram of a patient's heart can be used to assess cardiac performance by validating the existence of cardiac abnormalities, such as, arrhythmias evinced by an abnormally fast heart rate (e.g., tachycardia), an abnormally slow heart rate (e.g., bradycardia), or a normal rate but the depolarization is abnormally propagated (e.g., ectopic, or conduction system defect). The existence of an arrhythmia typically indicates that the heart's rhythm initiation and/or conduction system is functioning abnormally. CRT can be used, among other applications, to treat abnormal electrical conduction. In particular, CRT can be used to deliver electrical stimulation to portions of the heart 100 (FIG. 1) to resynchronize the heart's activation, thereby, improving the efficiency of atrial and ventricular contractions necessary to circulate blood throughout the body. The amount of benefit derived from CRT, however, typically varies depending upon the severity of the abnormality of the heart's conduction system. Therefore, prior to treating a patient using CRT, it is preferable to evaluate whether the heart's 100 (FIG. 1) conduction system is normal or abnormal.

The heart's ventricular conduction system can be assessed through analysis of the duration of ventricular depolarization. Identification of patients who may have a positive response to CRT can be performed using the duration of ventricular depolarization (e.g., the width of the QRS complex as shown in FIG. 3) measured from an intracardiac electrogram. For example, if the duration of ventricular depolarization is greater than a given threshold, then the patient may be considered a responder to CRT, and the CRT device for that patient may be configured appropriately. Patients are referred to as responders because they have an abnormal conduction system that can benefit from CRT.

Once the patient has been deemed a responder or non-responder, the CRT device can be configured to stimulate the heart to produce an atrioventricular delay of a duration appropriate for the patient type as is discussed below. For responders, the atrioventricular delay is generally set to about one-half of the intrinsic, or naturally occurring atrioventricular delay. For non-responders, the atrioventricular delay is set to approximately the intrinsic atrioventricular delay, such as the intrinsic atrioventricular delay minus a relatively small delay factor of about 30 milliseconds. One with ordinary skill in the art will recognize that other atrioventricular delay settings for responders and non-responders are possible as well. The atrioventricular delay is generally considered to be the length of time between an atrial sensed (or stimulated) event and the delivery of a ventricular output pulse.

Figure 7:
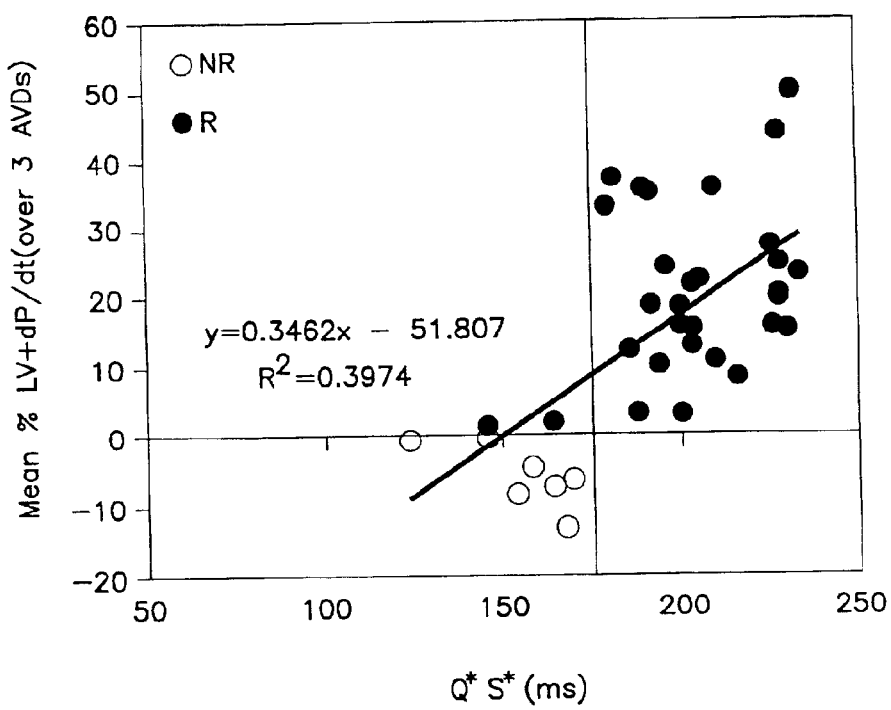
FIG. 7 is a graph illustrating mean percentage change in left ventricular pressure (LV+dp/dt) resulting from application of CRT plotted against the duration of intrinsic ventricular depolarization for responders and non-responders.

FIG. 7 shows a graph of the mean percent change in peak left ventricle pressure "LV dp/dt" after application of CRT over three atrioventricular delays for a group consisting of both responders and non-responders. Responders may be defined as those who receive an increase in peak left ventricle pressure when CRT is applied. From the graph, one can see that a relationship exists between the intrinsic Q*S* depolarization interval and the increase in peak left ventricle pressure due to CRT. For those having a relatively long intrinsic ventricular depolarization, CRT caused a relatively large increase in peak left ventricle pressure. For those having a relatively short intrinsic ventricular depolarization, CRT caused a relatively small increase or in some instances a decrease in peak left ventricle pressure.

A linear regression of the test cases shows that the correlation of percent change in peak left ventricle pressure to Q*S* is defined by the equation y=0.3462x −51.807, with a coefficient of determination $R^2$=0.3974. The vertical line of FIG. 7 indicates that an appropriate Q*S* threshold for distinguishing responders from non-responders is approximately 175 milliseconds for humans. The determination of 175 milliseconds as an appropriate threshold is further supported by the plot in FIG. 8.

Figure 8:
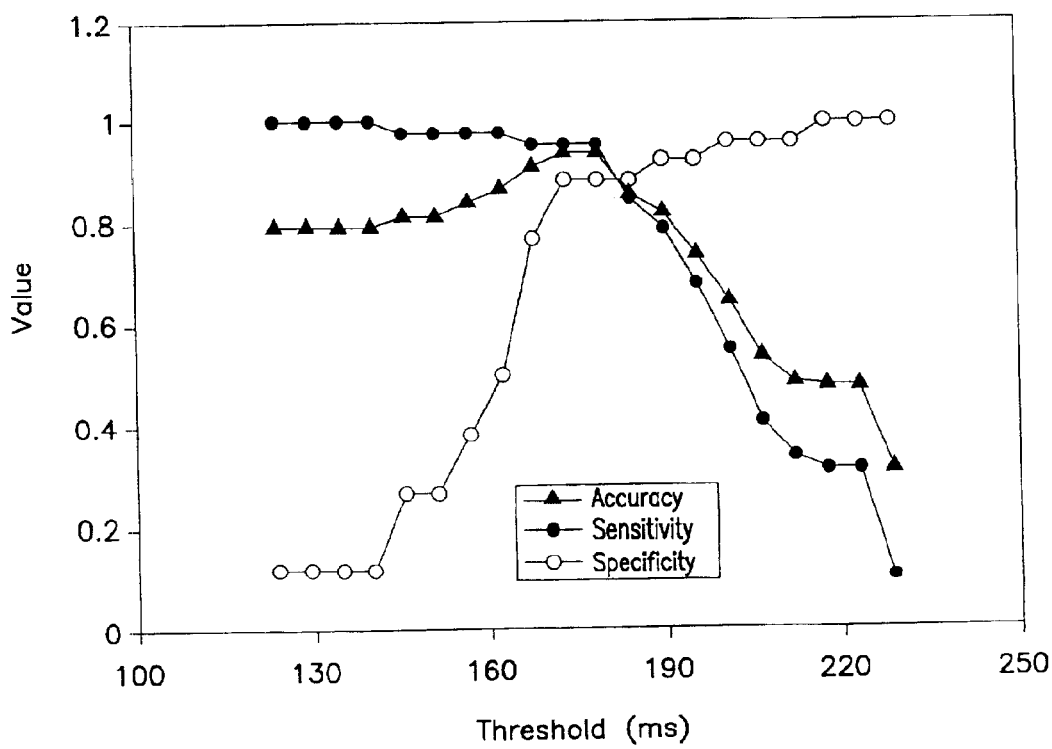
FIG. 8 is a graph illustrating the accuracy, sensitivity, and specificity of the separation between responders and non-responders for various thresholds of ventricular depolarization duration used to make the distinction.

FIG. 8 shows the values for the accuracy which represents the probability of correct classification of either a responder or non-responder, sensitivity which represents the probability of correct classification of patients as responders, and specificity which is the probability of correct classification of patients as non-responders plotted against Q*S* thresholds for humans. From this plot, it can be seen that the optimal threshold is about 175 milliseconds for humans because at this point the accuracy and sensitivity are above 0.95 and the specificity is above 0.88.

Figure 9:
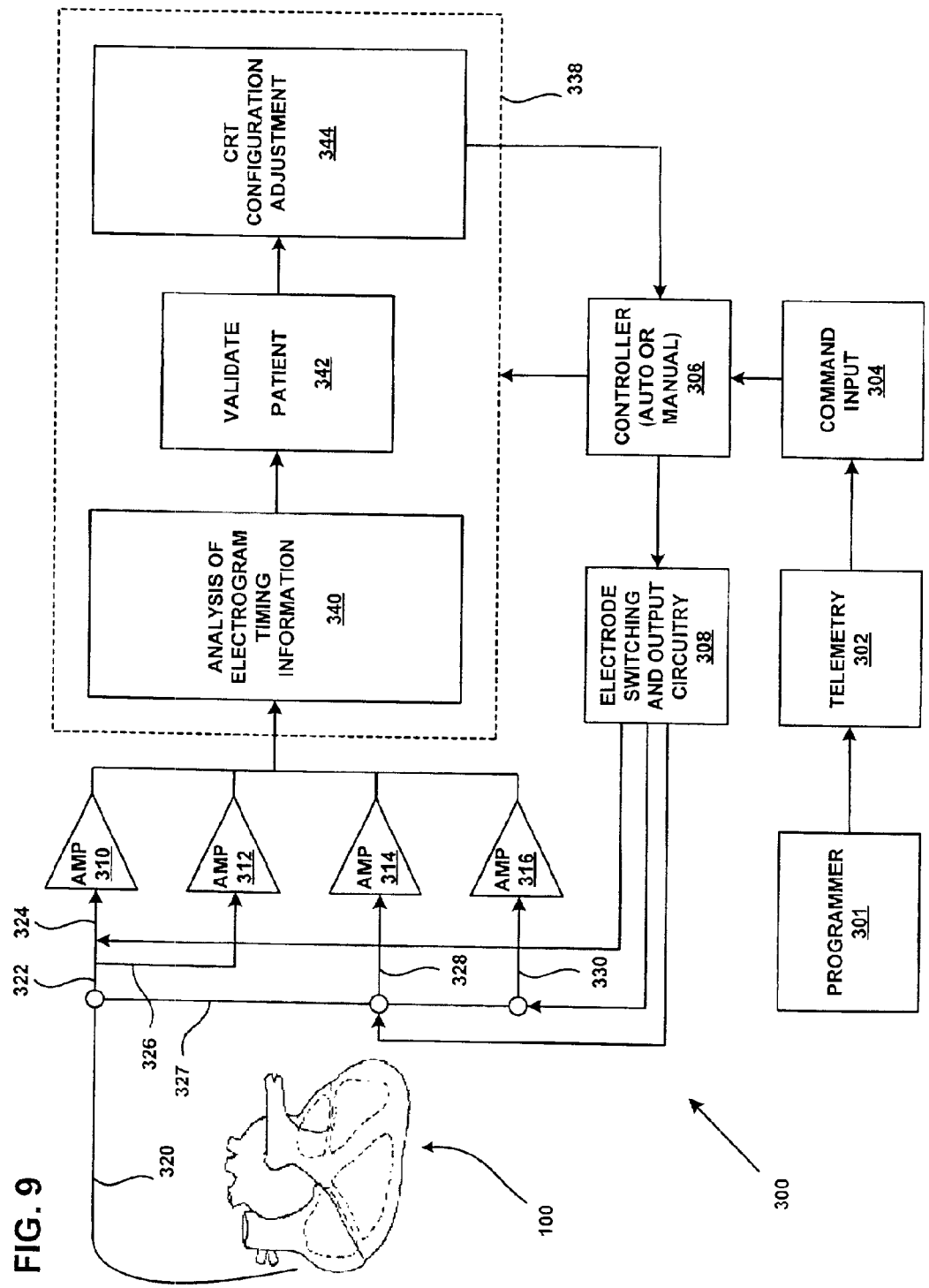
FIG. 9 illustrates one possible embodiment of a system that can be used to detect whether a patient is a responder to CRT.

One possible embodiment of a CRT system 300 that can be used to implement the methods for determining whether a patient is a responder is illustrated in FIG. 9. As shown in FIG. 9, the CRT system 300 generally comprises a programming device 301 that can be used to regulate stimulation pulses that are delivered to the heart 100. In one possible embodiment, the heart 100 is connected to various leads 320 having electrodes (not shown) and terminal pins (not shown) that can connect the heart 100 to the CRT system 300. The various leads 320 connecting the heart 100 to the CRT system 300 will be described in greater detail below.

The programmer 301 can regulate the stimulation pulses delivered to the heart 100 using, for example, a telemetry module 302. In one possible embodiment, the telemetry module 302 is unidirectional (e.g., capable of allowing the programmer 301 to receive data). However, in an alternative embodiment, the telemetry module 302 is bi-directional (e.g., capable of allowing the programmer 301 to receive and/or send data). The command input module 304 is configured to interpret the data received from the programmer 301 such that the stimulation pulses can be accurately distributed according to predetermined criteria, such as, the specific requirements of the patient being treated.

A controller 306 can be used to control the specific instructions regarding the stimulation pulses delivered to the heart 100. In one possible embodiment, the controller 306 can be controlled manually. In an alternative embodiment, however, the controller 306 can be controlled automatically using, for example, feedback received from an intrinsic signal analyzer 338. Moreover, one having ordinary skill in the art will readily appreciate that the controller 306 and the programmer 301 can be combined into a single unit. The instructions from the controller 306 are received by an electrode switching and output circuitry module 308 that delivers the stimulation pulses to the appropriate lead 320 within the heart 100.

As discussed above, the heart 100 is connected to the CRT system 300 using various leads 320. The various leads 320 are preferably configured to carry the CRT stimuli from the CRT device to the heart 100. Moreover, the various leads 320 can likewise operate in a demand mode, thereby, relaying intrinsic cardiac signals from the heart's 100 electrical conduction system back to one or more sense amplifiers 310, 312, 314, 316. In one possible embodiment, the various leads 320 comprise separate and distinct leads connecting the CRT system 300 to different portions of the heart 100. In particular, the various leads 320 can comprise a lead 322 connected to the right-side portion or pump 102 (FIG. 1) of the heart 100, including, for example, a right atrium lead 324 configured to operate with a right atrium amplifier 310 and a right ventricle lead 326 configured to operate with a right ventricle amplifier 312. Similarly, the various leads 320 can comprise a lead 327 connected to the left-side portion or pump 104 (FIG. 1) of the heart 100, including, for example, a first left ventricle lead 328 configured to operate with a first left ventricle amplifier 314 and a second left ventricle lead 330 configured to operate with a second left ventricle amplifier 316.

As discussed above, the various leads 320 connected to the heart 100 can relay intrinsic cardiac signals from the heart's 100 electrical conduction system back to the one or more sense amplifiers 310, 312, 314, 316. The intrinsic cardiac signals amplified by the sense amplifiers 310, 312, 314, 316 can then be processed by an intrinsic signal analyzer 338 incorporated in whole or in part by an implantable heart stimulation device (i.e., CRT device) or a device programmer. The intrinsic signal analyzer 338 generally can comprise a detection module 340 that is configured to analyze the intracardiac electrogram information to detect the beginning and ending of ventricular depolarization, such as the Q* and S* values discussed above with reference to FIG. 3.

Calculating Q* and S* from the intracardiac electrogram signal may be done in various ways. See for example, the calculation of Q* from U.S. Pat. No. 6,144,880, which is commonly assigned to Cardiac Pacemakers, Inc. and is incorporated herein by reference. In one embodiment, calculating Q* and S* may proceed as follows. For Q*, a waveform V(n) including the QRS complex must be acquired and analyzed, such as by the detection module 340 of the CRT device or CRT device programmer. The acquisition involves digitizing the waveform V(n) including the activity beginning at the time of an atrial reference marker indicating the end of atrial activity and extending beyond the QRS complex received by the electrode in the left or right ventricle and storing it in memory of the CRT device or CRT device programmer. Then, Q* is found by the following process.

First, the detection module 340 smooths the waveform V(n). This may be done by smoothing the waveform V(n) seven times using a 5 point rectangular moving window (for a sampling frequency of 500 Hz) whereby the 5 samples for each window are averaged and the average is assigned to the middle sample of the five. A derivative $dV(n)/dt$ of the smoothed waveform is taken, and the absolute value of the derivative $dV(n)/dt$ is normalized to range from 0 to 1.

The time samples n from the atrial reference marker time $T_P$ to the time $T_R$ of the peak of the R wave of the QRS complex are analyzed. This analysis involves calculating the mean and standard deviation of both the smoothed waveform V(n) and the normalized absolute value of its derivative $dV(n)/dt$ for each time sample within a 50 ms moving window. The baseline window with the minimum mean (i.e., baseline mean) plus a baseline standard deviation for |dv (n)/dt| is found and its values are used in the following steps.

For each sample n between $T_P$ and $T_R$ if the baseline mean is less than |dV(n)/dt|, but more than or equal to |dV(n)/dt|, then the number of data points N in another 50 ms window is found. N is the accumulation of each data point nw where |dv(nw)/dt| is greater than the baseline mean plus the baseline standard deviation. The window sample nw of this other window ranges from n to n plus the total number of data points in the window.

If N divided by the total number of data points in the window is greater than 0.96 and $T_q=0$, then set $T_q$ equal to n0−1, where $T_q$ is the current result of sample time for Q* and n0 is the time sample of the first data point that contributes to N. If the total number of data points in the window minus N is greater than or equal to 2, then $T_q$ is reset to zero. After this is completed for all values of n between $T_P$ and $T_R$, then the final value of $T_q$ is used as Q*. This process may be repeated to obtain a value of Q* for several beats, such as 16, and the median of these Q* values may be used in the computation of the ventricular depolarization interval. It may be desirable to include Q* values in the median determination for beats where the interval from R wave peak to R wave peak between beats has a variation within 10%.

For S*, the same process may be repeated but the time samples n ranging from the time $T_P+1$ which occurs after sensing atrial activity in the next cycle until the time $T_R$ of the peak of the R wave of the QRS complex of the current cycle are analyzed rather than the samples occurring prior to the R wave peak. Once the process discussed above has been completed for all values starting at $T_P+1$ and continuing to $T_R$ (i.e., working backwards through the samples with respect to time), the final value of $T_q$ is used as S*. As with Q*, this process for S* may be repeated to obtain a value of S* for several beats, such as 16, and the median of these S* values may be used in the computation of the ventricular depolarization interval.

After analysis of the electrogram information to find the beginning and ending of ventricular depolarization such as Q* and S*, a processing module 342 may compute the duration of depolarization and compare it to a threshold value, such as 175 milliseconds, in accordance with the method described below with reference to FIG. 10 to validate the patient as a responder or non-responder. A configuration module 344 can be used to make adjustments to the CRT system 300 based upon whether the processing module 342 determines the patient to be a responder or non-responder. The adjustments may include setting the atrioventricular delay of the CRT device to about one-half of the intrinsic value for responders or to approximately the intrinsic value for non-responders. For embodiments where the device programmer includes all or part of the intrinsic signal analyzer 338, the device programmer may send an instruction through telemetry 302 to the implanted heart stimulation device to set the atrioventricular delay.

The method of the present disclosure can be implemented using a CRT system as shown in FIG. 9 comprising various devices and/or programmers, including implantable or external CRT devices and/or programmers such as a CRT tachy or brady system. Accordingly, the method of the present disclosure can be implemented as logical operations controlling a suitable CRT device and/or programmer. The logical operations of the present disclosure can be implemented: (1) as a sequence of computer implemented steps running on the CRT device and/or programmer; and (2) as interconnected machine modules within the CRT device and/or programmer.

The implementation is a matter of choice dependant on the performance requirements of the CRT device and/or programmer implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

Figure 10:
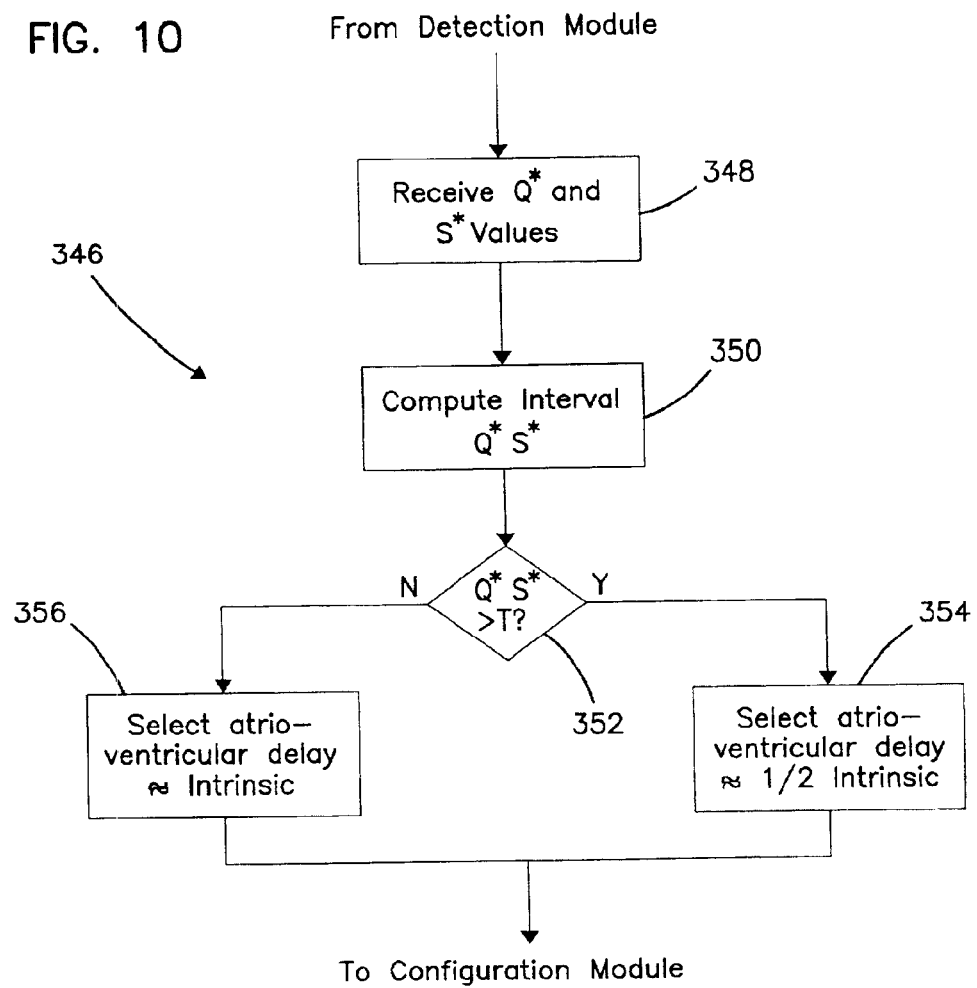
FIG. 10 is an operational flow summarizing the logical operations employed by an exemplary system for detecting whether a patient is a responder to CRT.

FIG. 10 shows an exemplary embodiment 346 of the logical operations of the processing module 342. The process begins by the processing module 342 receiving the Q* and S* values from the signals measured by detection module 340 at receive operation 348. At interval operation 350, the processing module 342 computes the time interval between the Q* and S* values. At query operation 352, the processing module 342 compares the Q*S* interval to the threshold, such as 175 milliseconds.

If the processing module 342 determines that Q*S* is greater than the threshold, then the processing module 342 selects an atrioventricular delay that is about one-half of the intrinsic atrioventricular delay at delay operation 354. If the processing module 342 determines that Q*S* is less than or equal to the threshold, then the processing module 342 selects an atrioventricular delay that is approximately equal to the intrinsic atrioventricular delay at delay operation 356. It is desirable at delay operation 356 to set the atrioventricular delay to the intrinsic atrioventricular delay value less a small delay factor of about 30 milliseconds. The configuration module 344 then implements the atrioventricular delay selected by processing module 342 when applying CRT or other pacing therapy to the patient.

While the invention has been particularly shown and described with reference to preferred embodiments thereof, it will be understood by those skilled in the art that various other changes in the form and details may be made therein without departing from the spirit and scope of the invention.

What is claimed is:

1. A method for determining whether a patient is a responder to resynchronization therapy, the method comprising:
   detecting a beginning of an intrinsic ventricular depolarization with an electrode positioned at a ventricle of the heart of the patient;
   detecting an ending of the intrinsic ventricular depolarization;
   measuring an interval between the beginning of the intrinsic ventricular depolarization and the ending of the intrinsic ventricular depolarization;
   comparing the interval to a threshold; and
   when the interval is greater than the threshold, setting a paced atrio-ventricular delay of the heart stimulation device to less than an intrinsic atrio-ventricular delay of the patient.

2. The method of claim 1, wherein the electrode that detects the beginning of the intrinsic ventricular depolarization detects the ending of the intrinsic ventricular depolarization.

3. The method of claim 1, wherein the electrode is positioned within a left ventricle.

4. The method of claim 1, wherein the threshold is 175 milliseconds.

5. The method of claim 1, wherein the steps of detecting the beginning and the ending of the intrinsic ventricular depolarization, measuring the interval, and comparing the interval are performed periodically other than for each cardiac cycle.

6. The method of claim 1, wherein the paced atrio-ventricular delay of the heart stimulation device is set to approximately one-half the intrinsic atrio-ventricular delay of the patient.

7. The method of claim 1, further comprising the step of:
   when the interval is less than the threshold, setting the paced atrio-ventricular delay of the heart stimulation device equal to approximately 30 milliseconds less than the intrinsic atrio-ventricular delay of the patient.

8. The method of claim 1, wherein the heart stimulation device performs the step of measuring the interval.

9. The method of claim 1, wherein the heart stimulation device performs the step of comparing the interval to the threshold.

10. The method of claim 9, wherein the device programmer performs the step of comparing the interval to the threshold.

11. The method of claim 1, wherein a device programmer is in communication with the electrode, and wherein the device programmer performs the step of measuring the interval.

12. The method of claim 1, wherein a device programmer is in communication with the heart stimulation device, the method further comprising:
   sending an instruction to the heart stimulation device to set the paced atrio-ventricular delay of the heart stimulation device.

13. The method of claim 1, wherein measuring an interval comprises statistical analysis of multiple intervals measured from multiple intrinsic ventricular depolarizations.

14. The method of claim 13, wherein the statistical analysis involves calculating a median of the multiple intervals.

15. The method of claim 1, wherein detecting the beginning and ending of the ventricular depolarization comprises detecting Q* and S*.

16. The method of claim 15, wherein Q* is computed by smoothing a depolarization signal and finding a point in time in a cardiac cycle prior to an R wave peak where a value of the smoothed depolarization first exceeds a baseline standard deviation value computed from the smoothed waveform and wherein S* is computed by finding a point in time after the R wave peak where a value of the smoothed depolarization last exceeds the baseline standard deviation value.

17. The method of claim 1, wherein the steps of detecting the beginning and the ending of the intrinsic ventricular depolarization, measuring the interval, and comparing the interval are performed by an implantable device.

18. A system for determining whether a patient is a responder to resynchronization therapy, the system comprising:
   an electrode adapted to be positioned at a ventricle of the heart of the patient;
   a detection module communicatively linked to the electrode, wherein the detection module detects a beginning of an intrinsic ventricular depolarization and an ending of the intrinsic ventricular depolarization; and
   a processing module communicatively linked to the detection module, wherein the processing module computes an interval between the beginning of the intrinsic ventricular depolarization and the ending of the intrinsic ventricular depolarization and compares the interval to a threshold.

19. The system of claim 18, wherein the detection module and the processing module are contained in an implantable device.

20. The system of claim 18, wherein the detection module detects the beginning of the intrinsic ventricular depolarization and the ending of the intrinsic ventricular depolarization from an electrical signal received from the electrode.

21. The system of claim 18, wherein the electrode is positionable within a left ventricle.

22. The system of claim 18, wherein the threshold is 175 milliseconds.

23. The system of claim 18, wherein the detection module detects the beginning and ending of the ventricular depolarization and the processing module computes the interval and compares the interval to a threshold periodically other than for each cardiac cycle.

24. The system of claim 18, wherein the paced atrio-ventricular delay is set to one-half of the intrinsic atrio-ventricular delay of the patient.

25. The system of claim 18, wherein when the interval is less than the threshold, the heart stimulation device sets the paced atrio-ventricular delay to approximately 30 milliseconds less than the intrinsic atrio-ventricular delay.

26. The system of claim 18, wherein the detection module and processing module are contained in a device programmer that is in communication with a heart stimulation device that is electrically connected to the electrode, and wherein the device programmer sends an instruction to the heart stimulation device to set the paced atrio-ventricular delay of the heart stimulation device.

27. The system of claim 18, wherein the processing module statistically analyzes multiple intervals detected from multiple intrinsic ventricular depolarizations.

28. The system of claim 27, wherein the statistical analysis involves calculating a median of the multiple intervals.

29. The system of claim 18, the beginning of the ventricular depolarization is Q* and the ending of the ventricular depolarization is S*.

30. The system of claim 29, wherein Q* is computed by smoothing a depolarization signal and finding a point in time in a cardiac cycle prior to an R wave peak where a value of the smoothed depolarization first exceeds a baseline standard deviation value computed from the smoothed waveform and wherein S* is computed by finding a point in time after the R wave peak where a value of the smoothed depolarization last exceeds the baseline standard deviation value.

31. A system for determining whether a patient is a responder to resynchronization therapy, the system comprising:
   means for detecting a beginning of an intrinsic ventricular depolarization and an ending of the intrinsic ventricular depolarization; and
   means for computing an interval between the beginning of the intrinsic ventricular depolarization and the ending of the intrinsic ventricular depolarization and for comparing the interval to a threshold.

32. The system of claim 31, wherein the means of computing and for comparing computes the interval by statistically analyzing multiple intervals detected from multiple intrinsic ventricular depolarizations.

33. The system of claim 32, wherein the means for computing and for comparing statistically analyzes multiple intervals by calculating a median.

34. The system of claim 31, wherein the means for detecting detects the beginning of the intrinsic ventricular depolarization and the ending of the intrinsic ventricular depolarization from an electrical signal received from an electrode positionable at a ventricle.

35. The system of claim 31, wherein the electrode is adapted to be positioned within a left ventricle.

36. The system of claim 31, wherein the threshold is 175 milliseconds.

37. The system of claim 31, wherein the means for detecting detects the beginning and ending of the ventricular depolarization and the means for computing and comparing computes the interval and compares the interval to a threshold periodically other than for each cardiac cycle.

38. The system of claim 31, wherein the paced atrio-ventricular delay is set to one-half of the intrinsic atrio-ventricular delay of the patient.

39. The system of claim 31, wherein when the interval is less than the threshold, the heart stimulation device sets the paced atrio-ventricular delay to equal to approximately 30 milliseconds less than the intrinsic atrio-ventricular delay of the patient.

40. The system of claim 31, wherein the means for detecting and the means for computing and for comparing are contained in a device programmer that is in communication with a heart stimulation device, and wherein the device programmer sends an instruction to the heart stimulation device to set the paced atrio-ventricular delay of the heart stimulation device.

41. The system of claim 31, wherein the beginning of the ventricular depolarization is Q* and the ending of the ventricular depolarization is S*.

42. The system of claim 41, wherein Q* is computed by smoothing a depolarization signal and finding a point in time in a cardiac cycle prior to an R wave peak where a value of the smoothed depolarization signal first exceeds a baseline standard deviation value computed from the smoothed depolarization signal and wherein S* is computed by finding a point in time after the R wave peak where a value of the smoothed depolarization signal last exceeds the baseline standard deviation value.

43. The system of claim 31, wherein the means for detecting and the means for computing and comparing are contained in an implantable device.

* * * * *

UNITED STATES PATENT AND TRADEMARK OFFICE
CERTIFICATE OF CORRECTION

PATENT NO. : 6,993,389 B2
APPLICATION NO. : 10/008397
DATED : January 31, 2006
INVENTOR(S) : Ding et al.

It is certified that error appears in the above-identified patent and that said Letters Patent is hereby corrected as shown below:

Column 11,
Line 29, delete "threshold." and insert -- threshold, wherein the detection module and processing module are contained in a heart stimulation device that is electrically connected to the electrode, and wherein when the interval is greater than the threshold, the heart stimulation device sets a paced atrio-ventricular delay to less than an intrinsic atrio-ventricular delay of the patient. --.
Line 63, after "18," insert -- wherein --.

Column 12,
Line 16, delete "threshold." and insert -- threshold, wherein the means for detecting and means for computing and comparing are contained in a heart stimulation device that is electrically connected to an electrode, and wherein when the interval is greater than the threshold, the heart stimulation device sets a paced atrio-ventricular delay to less than an intrinsic atrio-ventricular delay of the patient. --.

Signed and Sealed this

Eleventh Day of July, 2006

JON W. DUDAS
*Director of the United States Patent and Trademark Office*